United States Patent
Kim et al.

(10) Patent No.: US 10,490,300 B2
(45) Date of Patent: Nov. 26, 2019

(54) METHODS AND APPARATUS FOR ASSESSING PATHWAYS FOR BIO-CHEMICAL SYNTHESIS

(71) Applicant: Samsung Electronics Co., Ltd., Suwon-si, Gyeonggi-do (KR)

(72) Inventors: Taeyong Kim, Daejeon (KR); Venkata Tadi Siva Kumar, Andhra Pradesh (IN); Varun Giri, Delhi (IN); Anirban Bhaduri, Bangalore (IN)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1002 days.

(21) Appl. No.: 14/984,190

(22) Filed: Dec. 30, 2015

(65) Prior Publication Data

US 2016/0196323 A1    Jul. 7, 2016

(30) Foreign Application Priority Data

Jan. 5, 2015   (IN) ............................... 81/CHE/2015
Feb. 9, 2015   (KR) ....................... 10-2015-0019727

(51) Int. Cl.
*G01N 33/48*   (2006.01)
*G01N 33/50*   (2006.01)
*G16C 20/10*   (2019.01)

(52) U.S. Cl.
CPC .................................. *G16C 20/10* (2019.02)

(58) Field of Classification Search
None
See application file for complete search history.

(56) References Cited

U.S. PATENT DOCUMENTS

| 6,498,242 | B1 | 12/2002 | Cheng et al. |
| 8,088,607 | B2 | 1/2012 | Burgard et al. |
| 2002/0142321 | A1 | 10/2002 | Palsson et al. |

OTHER PUBLICATIONS

Hatzimanikatis et al. Analysis and design of metabolic reaction networks via mixed-integer linear optimization. AIChE Journal, vol. 42, pp. 1277-1292. (Year: 1996).*
Cho et al., Prediction of novel synthetic pathways for the production of desired chemicals, *BMC Systems Biology*, 4(35): 2-16 (2010).
Rahman et al., EC-BLAST: A Tool to Automatically Search and Compare Enzyme Reactions, *Nat. Methods*, 11(2): 171-174 (2014).
Wicker et al., Predicting biodegradation products and pathways: a hybrid knowledge- and machine learning-based approach, *Bioinformatics*, 26(6): 814-821 (2010).

* cited by examiner

*Primary Examiner* — Russell S Negin
(74) *Attorney, Agent, or Firm* — Leydig, Voit & Mayer, Ltd.

(57) ABSTRACT

In a method of assessing a bio-chemical synthesis pathway, input data (that is, data representing a chemical pathway, a reaction, and/or a molecule) is processed to extract a feature of at least one selected from an association of a molecular substructure, an association of at least one molecular substructure classified according to a molecular transformation type, and an association of a reaction transformation type. The input data may be ranked or filtered based on an association measure extracted from a chemical knowledge-base (e.g., database storing chemical data), thereby enabling a prediction or selection of an appropriate chemical pathway, reaction, and/or molecule.

20 Claims, 6 Drawing Sheets

METHODS AND APPARATUS FOR ASSESSING PATHWAYS FOR BIO-CHEMICAL SYNTHESIS

RELATED APPLICATION

This application claims the benefit of Indian Patent Application No. 81/CHE/2015, filed on Jan. 5, 2015, in the Indian Intellectual Property Office and Korean Patent Application No. 10-2015-0019727, filed on Feb. 9, 2015, in the Korean Intellectual Property Office, the disclosures of which are each incorporated herein in its entirety by reference.

BACKGROUND

1. Field

The present disclosure relates to methods of assessing chemical pathways, reactions, and molecules, and more particularly, to methods of and apparatus for selecting an appropriate chemical pathway, reaction, and molecule chemical by assessing the chemical pathway, reaction, molecule, or a combination thereof based on a chemical knowledgebase.

2. Description of the Related Art

There are many possibilities of synthesizing a molecule through organic design. As known from chemical retrosynthetic approaches, a molecule can be synthesized from multiple precursors. Also, as the number of synthesis steps increases, the possibilities of potential start compounds (precursors) increase exponentially.

SUMMARY

Provided are methods and apparatuses for assessing a chemical pathway, reaction, and molecule so as to select a realizable chemical pathway, reaction, and molecule.

Provided is a non-transitory computer-readable storage medium having recorded thereon a program for causing a computer to execute the methods described herein. The technical problems to be solved by the present embodiments are not limited to the technical problems described above; yet, another technical problem can be inferred from the following embodiments.

Additional aspects will be set forth in part in the description which follows and, in part, will be apparent from the description, or may be learned by practice of the presented exemplary embodiments.

According to an aspect of an exemplary embodiment, a method of assessing a chemical pathway, reaction, and molecule includes processing input data; extracting a feature from the processed input data; obtaining an association measure coefficient based on chemical knowledgebase; and assessing the processed input data based on the obtained association measure coefficient, wherein the input data and the chemical knowledgebase include at least one chemical pathway, at least one reaction, and at least one molecule.

The processing of input data may include at least one of identifying a reaction transformation for the at least one reaction included in the input data, and classifying the at least one reaction based on an at least one reaction transformation type; identifying a molecular transformation for the at least one molecule included in the input data, and classifying the at least one molecule based on an at least one molecular transformation type; and identifying a molecular substructure contained in the at least one molecule included in the input data.

The extracted feature may include an association of a molecular substructure, an association of a molecular substructure classified according to a molecular transformation type, and an association of a reaction transformation type.

The obtaining of an association measure coefficient based on chemical knowledgebase may include processing the chemical knowledgebase; extracting a feature from the processed chemical knowledgebase, wherein the feature contains at least one of an association of a molecular substructure, an association of a molecular substructure classified according to a molecular transformation type, and an association of a reaction transformation type; and obtaining the association measure coefficient based on a feature extracted from the processed chemical knowledgebase and a feature extracted from the processed input data.

The processing of the chemical knowledgebase may include at least one of identifying a reaction transformation for at least one reaction included in the chemical knowledgebase and classifying the at least one reaction based on at least one reaction transformation type; identifying a molecular transformation for at least one molecule included in the chemical knowledgebase and classifying the at least one molecule based on at least one molecular transformation type; and identifying a molecular substructure contained in the at least one molecule included in the chemical knowledgebase.

The molecular transformation, for the at least one molecule included in the input data, may include at least one molecule substructure residing on the at least one molecule included in the input data and at least one of a bond change, a bond rearrangement, and a chemical state change that occurs during a reaction process on the at least one molecule included in the input data.

The reaction transformation, for the at least one reaction included in the input data, may include a set of molecular transformations of the at least one molecule participating in a reaction included in the input data.

The molecular transformation, for the at least one molecule included in the chemical knowledgebase, may include at least one molecule substructure residing on the at least one molecule included in the chemical knowledgebase and at least one of a bond change, a bond rearrangement, and a chemical state change that occurs during a reaction process on the at least one molecule included in the chemical knowledgebase.

The reaction transformation, for the at least one reaction included in the chemical knowledgebase, may include a set of molecular transformations of the at least one molecule participating in a reaction included in the chemical knowledgebase.

The association of a molecular substructure, among the feature extracted from the input data, is derived from at least one of an occurrence of at least one molecular substructure and a co-occurrence of the at least one molecular substructure, wherein the co-occurrence is recorded with a relative distance between the molecular substructures.

The association of a reaction transformation type, among the feature extracted from the input data, is derived from at least one of an occurrence of at least one reaction transformation type and a co-occurrence of the at least one reaction transformation type.

The association of a molecular substructure, among the feature extracted from the chemical knowledgebase, is derived from at least one of an occurrence of at least one molecular substructure and a co-occurrence of the at least one molecular substructure, wherein the co-occurrence is recorded with a relative distance between the molecular substructures.

The association of a reaction transformation type, among the feature extracted from the chemical knowledgebase, is derived from at least one of an occurrence of at least one reaction transformation type and a co-occurrence of the at least one reaction transformation type.

The assessing of the input data may include assigning a score to at least one feature extracted from the input data based on the obtained association measure coefficient; and computing a composite score, based on the assigned score, for at least one of the at least one chemical pathway, the at least one reaction, and the at least one molecule in the input data.

The assessing of the input data may include assigning a rank, according to the computed composite score, to at least one of the at least one chemical pathway, the at least one reaction, and the at least one molecule in the input data.

The assessing of the input data may include selecting at least one of the chemical pathway, the reaction, and the molecule, of which the composite score is greater than a threshold value in the input data.

According to an aspect of an exemplary embodiment, an apparatus includes a memory and at least one processor operatively coupled to the memory, wherein the processor include: a processing module configured to process input data; a feature extracting module configured to extract a feature from the processed input data; a module configured to obtain an association measure coefficient an association measure coefficient from chemical knowledgebase; and an analyzing assessment module configured to analyze the input data based on the association measure coefficient to assess the input data.

A non-transitory computer-readable recording medium having recorded thereon a program for causing a computer to execute the methods described herein.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
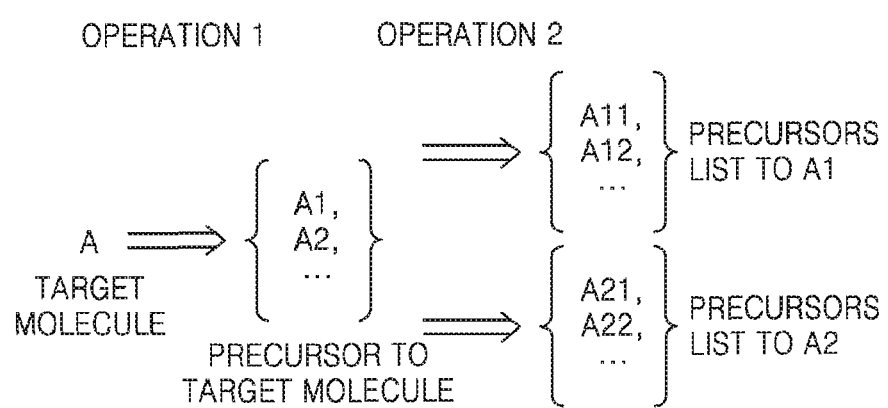
FIG. 1 illustrates a schema for chemical retro-synthesis.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

The advantages and features of the inventive concept and methods of achieving the advantages and features will be described more fully with reference to the accompanying drawings, in which exemplary embodiments of the inventive concept are shown. The inventive concept may, however, be embodied in many different forms and should not be construed as being limited to the exemplary embodiments set forth herein; rather these exemplary embodiments are provided so that this disclosure will be thorough and complete, and will fully convey the concept of the inventive concept to one of ordinary skill in the art.

Most of the terms used herein are general terms that have been widely used in the technical art to which the inventive concept pertains. However, some of the terms used herein may be created to reflect the intentions of technicians in this art, precedents, or new technologies. Also, some of the terms used herein may be arbitrarily chosen by the present applicant. In this case, these terms are defined in detail below. Accordingly, the specific terms used herein should be understood based on the unique meanings thereof and the whole context of the inventive concept.

Throughout the specification, when a portion "includes" or "consists of" an element, another element may be further included, rather than excluding the existence of the other element, unless otherwise described.

Hereinafter, the singular forms "a", "an" and "the" are intended to include the plural forms as well, unless expressly stated otherwise. For example, a "molecule", a "pathway", a "reaction", and a "molecular substructure" may each include at least one molecule, at least one pathway, at least one reaction, and at least one molecular substructure.

Hereinafter, exemplary embodiments will be described in detail with reference to the accompanying drawings. However, the constitution in the embodiments and drawings is merely exemplary, and thus this is not intended to limit the inventive concept to particular modes of practice, and it is to be appreciated that all changes, equivalents, and substitutes that do not depart from the spirit and technical scope of the inventive concept are encompassed in the inventive concept.

According to an exemplary embodiment, a method of and apparatus for assessing input data that includes a chemical pathway, a reaction, and/or a molecule by ranking and/or filtering the input data is provided. The assessment may be performed based on information or data from a chemical knowledgebase.

The chemical knowledgebase may include data regarding features such as known chemical pathways, reactions, and/or molecules. In brief, a set of features representing structural and chemical properties may be extracted from the input data based on similar features extracted from the chemical knowledgebase, in order to determine a ranking or score for a chemical pathway, reaction and/or molecule that is present in the input data.

The chemical knowledgebase includes a database (physical storage and associated database management system and software) storing the chemical data, such as data regarding known chemical pathways, reactions, and/or molecules. A goal of an assessing method is to assign a rank to the extracted features based on a propensity (to occur or exist) of the feature in the chemical knowledgebase. This facilitates assessment or selection of a pathway, a reaction, and/or a molecule present in the input data that represent a transformation and/or a structure that is likely to be more feasible. The database making up the chemical knowledgebase may be a single physical database, or it may be multiple physical databases presented as a single logical database.

FIG. 1 illustrates a schema for chemical retro-synthesis. Possible precursors to synthesize target molecule A are shown in FIG. 1. A1, A2, and the like represent precursors that may form target molecule A in one operation of a chemical synthesis. Similarly A11, A12 and the like represent precursors that may form target molecule A in two operations via precursor A1. Pathways for synthesis of target molecule A may be constructed using the shown precursors.

As a number of chemical synthesis operation increases, an exponential rise in possible pathways for synthesizing the target molecule A may also occur. Therefore, it is often challenging to assess experimentally all synthesis pathways reported using existing methods, such as retro-synthesis.

Figure 2:
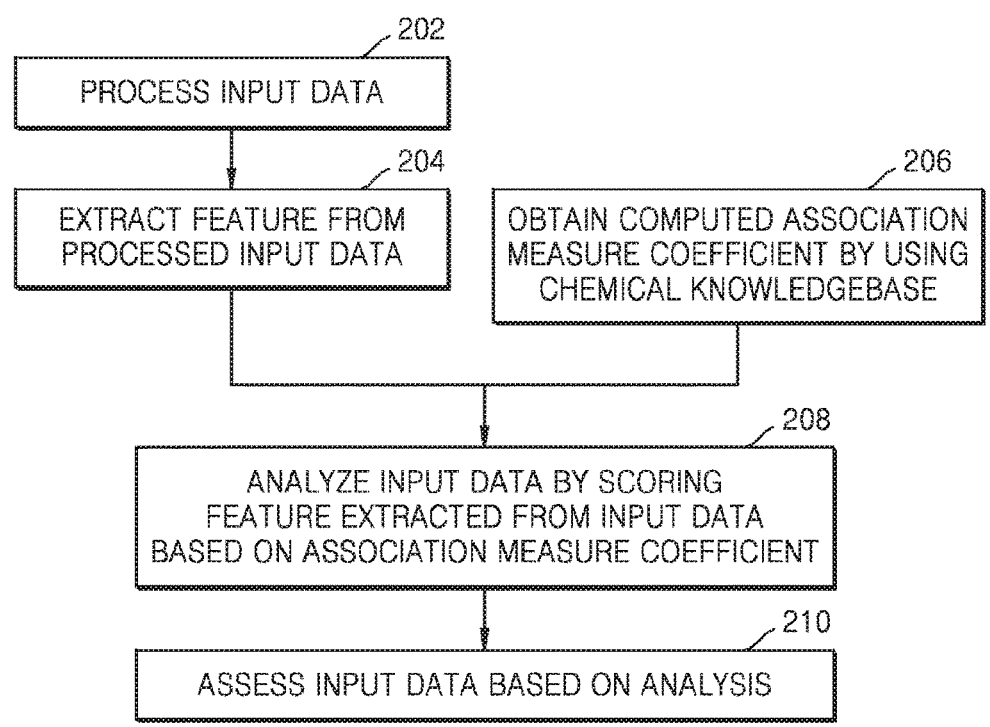
FIG. 2 is a flowchart of a method of assessing input data based on a chemical knowledgebase, according to an embodiment.

FIG. 2 is a flowchart of a method of assessing input data based on data from a chemical knowledgebase, according to an embodiment.

In operation 202, the input data may be received and processed to identify a structural and/or chemical attribute or feature, such as but not limited to, a reaction and molecular transformation, a transformation type, and a molecular substructure.

In operation 204, a feature may be extracted from the processed input data.

In operation 206, an association measure coefficient, which is computed based on data from the chemical knowledgebase, may be obtained. Operation 206 may be performed independently of operation 202 and operation 204.

In operation 208, the input data may be analyzed by scoring features extracted from the input data based on an association measure coefficient.

Finally in operation 210, the input data may be assessed based on the analysis performed in operation 208.

The assessment may involve ranking and/or filtering a chemical pathway, a reaction, and/or a molecule in the input data.

Hereinafter, each operation of FIG. 2 will be described in more detail.

1. Processing Input Data (Operation 202)

The chemical pathway, reaction, and/or molecule of the input data may be processed to identify and tabulate the structural and/or chemical attribute(s). The input data is processed to identify a reaction transformation and subsequently a reaction transformation type for the reaction, a molecular transformation and subsequently a molecular transformation type for the molecule participating in the reaction, and/or a substructure contained in the molecule. Processed information may be created and/or stored into a table (e.g., in memory 502 of FIG. 5) at this point, and may be used for extracting association information in operation 204.

As used herein, the molecular substructure refers to a connected structure whose atoms are a subset of the molecule. The molecular transformation may include a molecular substructure and a bond change, a bond rearrangement, and/or a chemical state change that occurs during a reaction process. A set of molecular transformations having common characteristics define a molecular transformation type. A molecule in a reaction may be classified according to a molecular transformation type thereof.

The reaction transformation may include a set of molecular transformations of at least one molecule participating in a reaction. Further, the set of reaction transformations having common characteristics define a reaction transformation type. A possible reaction of input data may be classified according to a reaction transformation type thereof.

2. Extraction of Features from Processed Input Data (Operation 204)

The structural and/or chemical attribute identified by processing the input data in operation 202 may be used for extraction of a feature. The extracted feature may include an association of the molecular substructure, an association of the molecular substructure classified with respect to the molecular transformation type, and/or an association of the reaction transformation type.

A feature containing the association of the molecular substructure may be related to the propensity of existence and/or coexistence of the structural feature on a molecule. The feature containing the association of the molecular substructure may be derived from an occurrence and/or a co-occurrence of the molecular substructure of the molecule present in the input data. The co-occurrence may be recorded with a relative distance between the molecular substructures. In addition the association of the molecular substructure may be classified with respect to a molecular transformation type thereof.

A feature containing the association of the reaction transformation type may be related to a propensity of existence and/or coexistence of a reaction transformation type in a reaction pathway. The feature containing the association of the reaction transformation type may be derived from an occurrence and/or a co-occurrence of the reaction transformation type of the reaction forming a pathway.

3. Obtaining Computed Association Measure Coefficient by Using the Chemical Knowledgebase (Operation 206)

An association measure coefficient may represent an aggregated structural and/or chemical attribute of the chemical knowledgebase. The coefficient may be computed based on the feature extracted from the chemical knowledgebase. Operations for computing the association measure coefficient will be described in detail below with reference to FIG. 3. The coefficient may be retrieved in operation 206 and may be used for analyzing input data through the association measure coefficient.

4. Analyzing Input Data by Scoring Feature Extracted from Bnput Data based on Association Measure (Operation 208)

The feature extracted from the input data (operation 204) and the association measure coefficient determined based on the chemical knowledgebase (operation 206) may be together used for the analysis of the input data. The feature extracted from the input data may be scored by using the association measure coefficient. Further, a composite score for the chemical pathway, the reaction, and/or the molecule in input data may be computed based on a score of the corresponding extracted feature.

5. Assessing Input Data (Operation 210)

The assessing of the input data may be performed by ranking and/or filtering the chemical pathway, the reaction, and/or the molecule based on the score assigned in operation 208.

The chemical pathway, the reaction, and/or the molecule present in the input data may be ranked based on the composite scores computed for the chemical pathway, the reaction, and/or the molecule in the input data.

Similarly, the filtering may be performed by selecting a chemical pathway, a reaction, and/or a molecule in the input data having an assigned composite score meeting or exceeding a defined threshold value.

Figure 3:
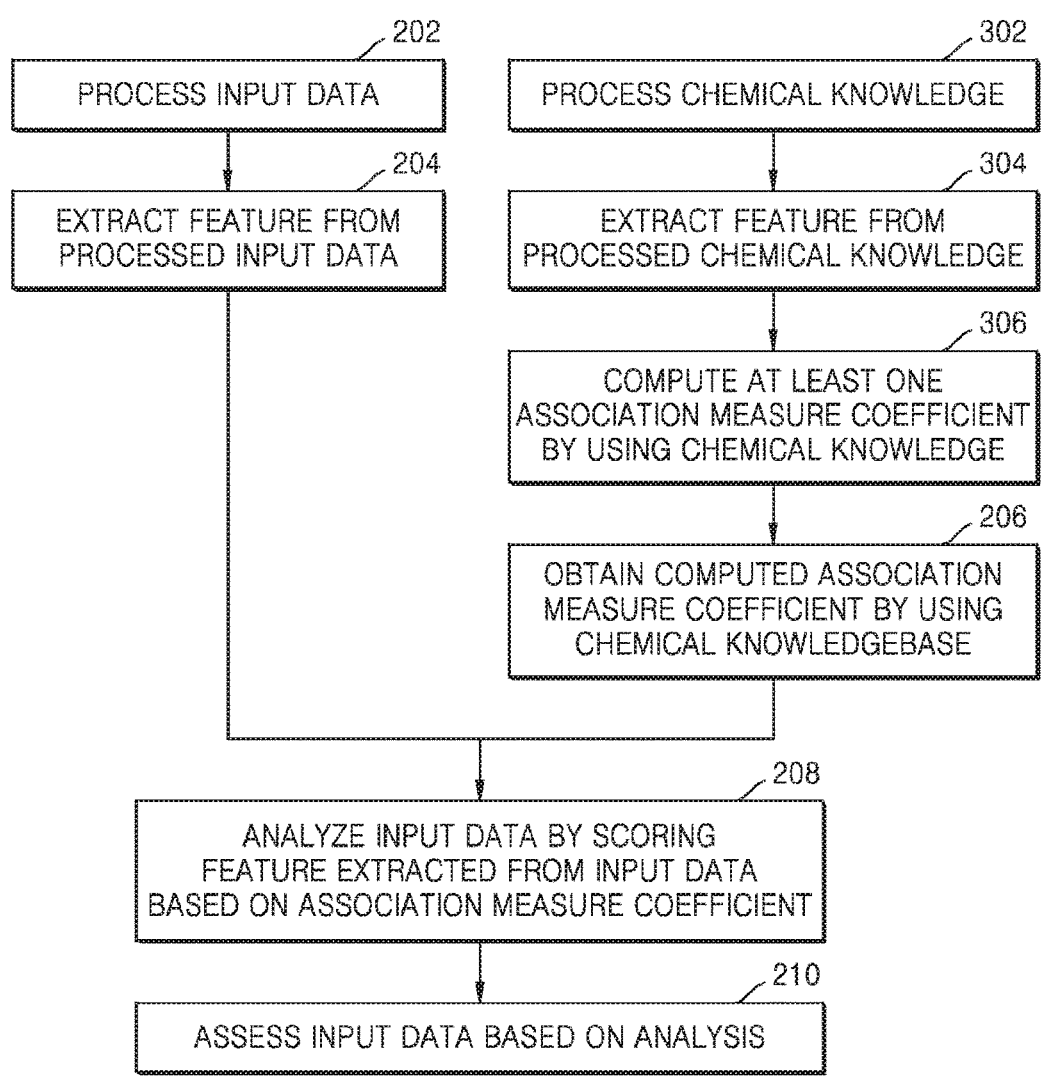
FIG. 3 illustrates a method of computing an association measure coefficient, according to an embodiment, based on the feature extracted from the chemical knowledgebase.

FIG. 3 illustrates a method of computing an association measure coefficient, according to an embodiment, based on the feature extracted from the chemical knowledgebase. Operations 202, 204, 206, 208, and 210 are described above with reference to FIG. 2. Further, operations 302 and 304 may be performed on the chemical knowledgebase in the same manner as for the input data in operation 202 and 204.

The association measure coefficient may be computed using the chemical knowledgebase at operation 306. The coefficient may be computed based on a feature extracted from the chemical knowledgebase using methods, such as, but not limited to, conditional probability, joint probability, and Bayesian statistics.

In one embodiment, the association measure coefficient may be computed using a feature containing an association of a molecular substructure, a feature containing an association of a molecular substructure classified with respect to the molecular transformation type, and/or a feature containing an association of the reaction transformation type.

Figure 4:
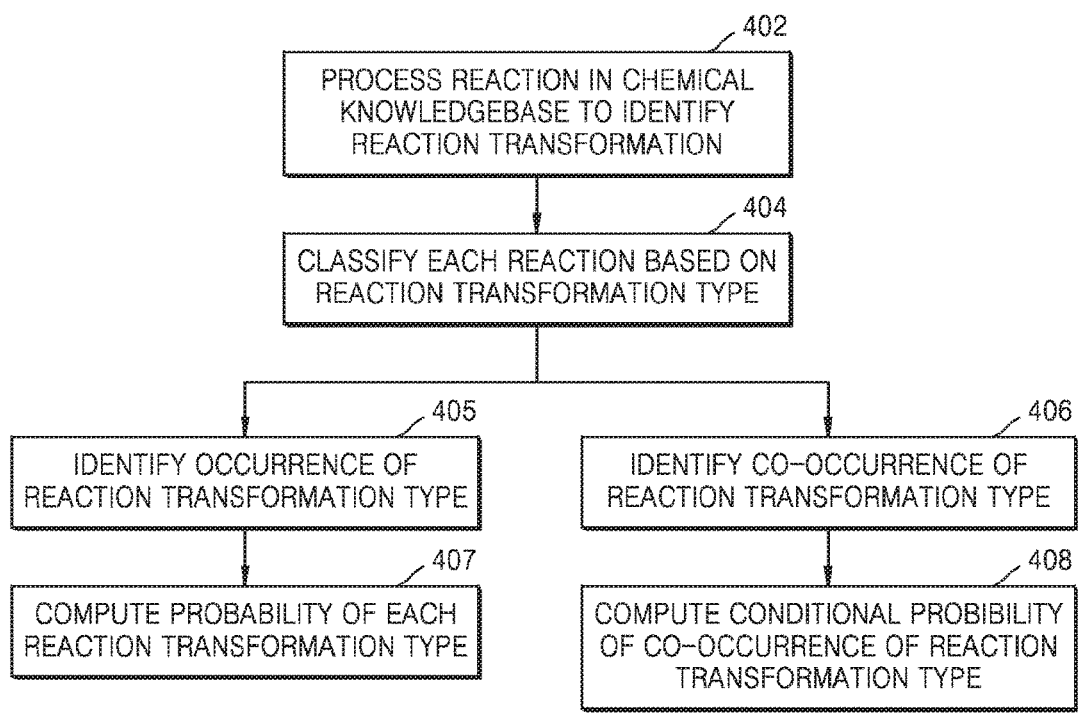
FIG. 4 is a flowchart of a method of computing an association measure coefficient based on features including associations of reaction transformation types, according an embodiment.

FIG. 4 illustrates a flowchart of a method of computing an association measure coefficient based on features including associations of reaction transformation types, according to an embodiment. First, the reaction contained in the chemical knowledgebase may be processed to identify a reaction transformation and classified into a reaction transformation type. The processing may be performed in the same manner as in operation 302.

FIG. 4 describes computation of two sets of association measure coefficients.

Computation 420 of a first set may be performed based on occurrences of a reaction transformation type, and may be defined as the probability of an occurrence of a specified reaction transformation type.

Computation 440 of a second set may be performed based on co-occurrences of a reaction transformation type pair in a reaction pathway. The association measure coefficients of the second set is defined as the joint probability between the reaction transformation types of two reactions in a reaction pathway.

In another embodiment, a feature extracted from the chemical knowledgebase at operation 304 and/or an association measure coefficient computed at operation 306 may be stored in a memory device (e.g., memory 502, or a different memory device such as a portable memory device) for future use, enabling a user to retrieve the stored data as and when desired.

Assessing input data containing a chemical pathway according to an embodiment will be described hereinafter.

First, the input data may be processed to identify a reaction transformation and subsequently a reaction transformation type for each reaction as in operation 202 of FIG. 2. Next, the feature containing occurrences and co-occurrences of the reaction transformation type within individual pathways may be extracted (operation 204). Association measure coefficients computed using a feature extracted from the chemical knowledgebase containing the association of reaction transformation type may be retrieved (operation 206). Computing of the coefficients is described above (FIG. 4). Features corresponding to each pair of reaction transformation types of reactions co-occurring in a pathway may be scored by association measure based on coefficients of joint probability of a co-occurrence. To score individual pathways, a composite score based on the average joint probability of a co-occurrence may be used. Finally, based on the score, the input chemical pathways may be assessed.

Figure 5:
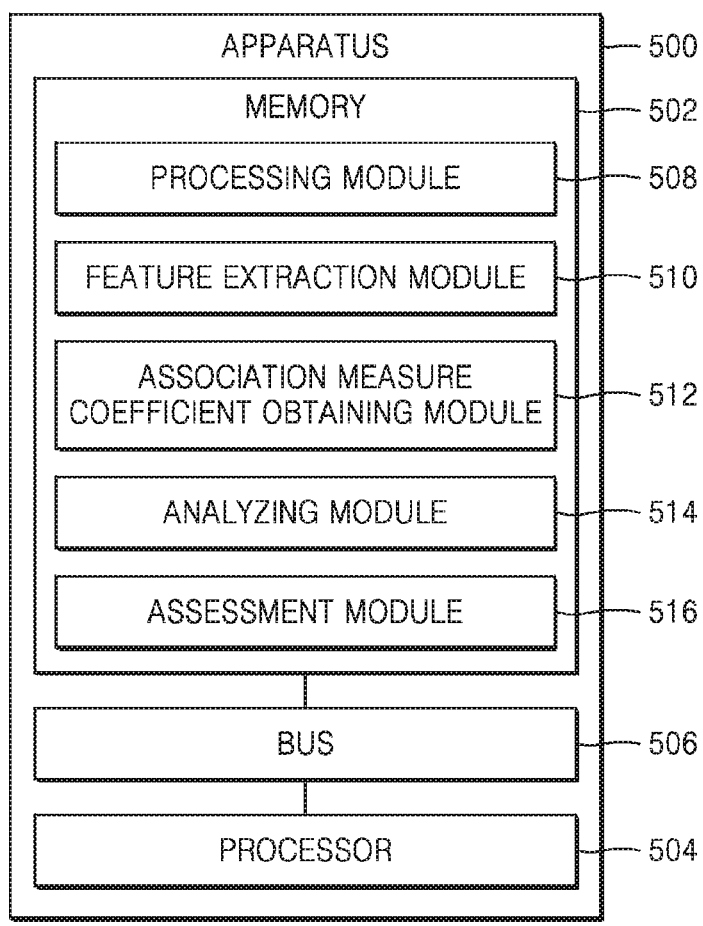
FIG. 5 is a block diagram of an apparatus according to an embodiment.

FIG. 5 is a block diagram of an apparatus for assessing input data based on a chemical knowledgebase, according to an embodiment.

The apparatus 500 may include a processor 504, and a memory 502 coupled to the processor 504.

The processor 504 may include a microprocessor, a microcontroller, a computational circuit, a complex instruction set computing (CISC) microprocessor, a reduced instruction set computing (RISC) microprocessor, a very long instruction word (VLIW) microprocessor, an explicitly parallel instruction computing (EPIC) microprocessor, a digital signal processor, any other type of processing circuit, or a combination thereof.

The memory 502 may include a computer memory element storing at least one module in the form of executable program which, when executed by the processor 504, instructs the processor 504 to perform the method operations illustrated in FIGS. 2 to 11. The memory 502 may include a processing module 508, a feature extraction module 510, an association measure coefficient obtaining module 512, an analyzing module 514, and an assessment module 516.

Computer memory elements may include any suitable memory devices or storage media for storing data and executable program, such as read only memory (ROM), random access memory (RAM), erasable programmable read only memory (EPROM), electrically erasable programmable read only memory (EEPROM), hard drive, or memory cards.

The apparatus 500 may operate in conjunction with program modules, including functions, procedures, data structures, and application programs, for performing tasks, defining abstract data types, or low-level hardware contexts. Executable program stored on any of the above-mentioned storage media may be executable by the processor 504.

The processing module 508 instructs the processor 504 to perform operation 202 of FIG. 2 and/or operation 302 of FIG. 3.

The feature extraction module 510 instructs the processor 504 to perform operation 204 of FIG. 2 and/or operation 304 of FIG. 3.

The association measure coefficient obtaining module 512 instructs the processor 504 to perform operation 206 (FIG. 2).

The analyzing module 514 instructs the processor 504 to perform operation 208 (FIG. 2).

The assessment module 516 instructs the processor 504 to perform operation 210 (FIG. 2).

In FIG. 5, the apparatus 500 is illustrated to have the analyzing module 514 and the assessment module 516 separately, but the analyzing module 514 and the assessment module 516 may be merged as an analyzing assessment module. The analyzing assessment module may instruct the processor to perform operation 208 of FIG. 2 and operations 208 and 210 of FIG. 2.

Figure 6:
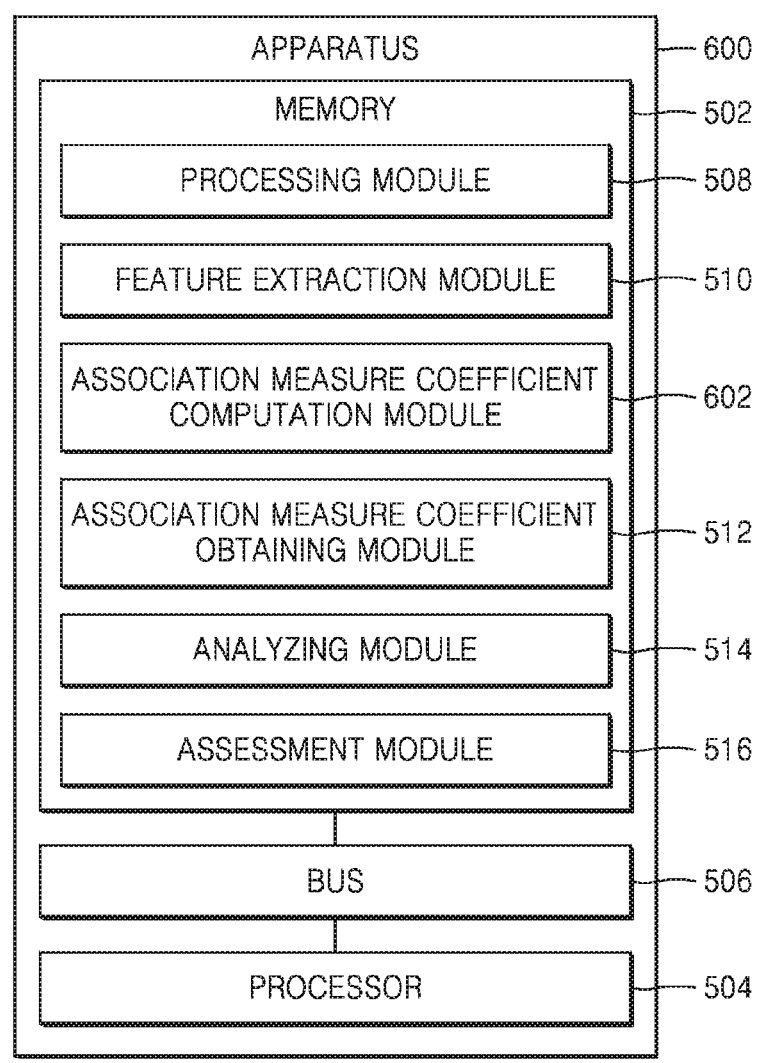
FIG. 6 is a block diagram of an apparatus for assessing input data based on a chemical knowledgebase, according to an embodiment.

FIG. 6 is a block level diagram of an apparatus 600 for assessing the input data based on the chemical knowledgebase and computing the association measure coefficient according to an embodiment. The apparatus 600 is configured to assess the input data with respect to the chemical knowledgebase in the same way as described in connection with FIG. 5. However, an additional feature of computing the association measure coefficient in absence of a computed association measure coefficient may be performed by a coefficient computation module 602, which instructs the processor 504 to perform operations 302, 304, and 306 (FIG. 3).

The present embodiments have been described with reference to specific example embodiments; it will be evident that various modifications and changes may be made to these embodiments without departing from the broader spirit and scope of the various embodiments. In other words, claims may be construed as including such replacements, modifications, and changes. Therefore, the content throughout the specification and drawings should be construed in a non-limiting sense.

The device described herein may include a processor, a memory for storing program data and executing it, a permanent storage unit such as a disk drive, a communications port for handling bi-directional communications with external devices (e.g., an internal/directly connected chemical knowledgebase and/or an external/remote chemical knowledgebase), and user interface devices, including a touch panel, keys, buttons, etc. When software modules or algorithms are involved, these software modules may be stored as program instructions or computer readable code executable on a processor on a computer-readable medium. Examples of the computer-readable medium include storage media such as magnetic storage media (e.g., read only memories (ROMs), random-access memory (RAMs), floppy discs, or hard discs), optically readable media (e.g., compact disk-read only memories (CD-ROMs) or digital versatile disks (DVDs)), etc. The computer readable recording medium can also be distributed over network coupled computer systems so that the computer readable code is stored and executed in a distributive manner. This media can be read by the computer, stored in the memory, and executed by the processor.

The exemplary embodiments may be described in terms of functional block components and various processing steps. Such functional blocks may be realized by any number of hardware and/or software components configured to perform the specified functions. For example, the exemplary embodiment may employ various integrated circuit (IC) components, e.g., memory elements, processing elements, logic elements, look-up tables, and the like, which may carry out a variety of functions under the control of one or more microprocessors or other control devices. Similarly, where the elements of the exemplary embodiment are implemented using software programming or software elements, the embodiment may be implemented with any programming or scripting language such as C, C++, Java, assembler language, or the like, with the various algorithms being implemented with any combination of data structures, objects, processes, routines or other programming elements. Functional aspects may be implemented in algorithms that are executed on one or more processors. Furthermore, the present invention could employ any number of conventional techniques for electronics configuration, signal processing and/or control, data processing and the like. The words "mechanism", "element", "means", and "configuration" are used broadly and are not limited to mechanical or physical embodiments, but can include software routines in conjunction with processors, etc. But can include software routines in conjunction with processors, etc.

The particular implementations shown and described herein are illustrative examples of the inventive concept and are not intended to otherwise limit the scope of the inventive concept in any way. For the sake of brevity, conventional electronics, control systems, software development and other functional aspects of the systems may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device.

The use of the terms "a" and "an" and "the" and similar referents in the context of describing the inventive concept (especially in the context of the following claims) are to be construed to cover both the singular and the plural. Furthermore, recitation of ranges of values herein are merely intended to serve as a shorthand method of referring individually to each separate value falling within the range, unless otherwise indicated herein, and each separate value is incorporated into the specification as if it were individually recited herein. Also, the steps of all methods described herein can be performed in any suitable order unless otherwise indicated herein or otherwise clearly contradicted by context. The inventive concept is not limited to the described order of the steps. The use of any and all examples, or exemplary language (e.g., "such as") provided herein, is intended merely to better illuminate the inventive concept and does not pose a limitation on the scope of the inventive concept unless otherwise claimed. Numerous modifications and adaptations will be readily apparent to one of ordinary skill in the art without departing from the spirit and scope.

In addition, other exemplary embodiments can also be implemented through computer readable code and/or instructions stored in or on a medium, e.g., a computer readable medium, to control at least one processing element to implement any above described exemplary embodiment. The medium can correspond to any medium or media permitting the storage and/or transmission of the computer readable code.

The computer readable code can be recorded/transferred on a medium in a variety of ways, with examples of the medium including recording media, such as magnetic storage media (e.g., ROM, floppy disks, hard disks, etc.) and optical recording media (e.g., CD-ROMs, or DVDs), and transmission media such as Internet transmission media. Thus, the medium may be such a defined and measurable structure including or carrying a signal or information, such as a device carrying a bitstream according to one or more exemplary embodiments. The media may also be a distributed network, so that the computer readable code is stored/transferred and executed in a distributed fashion. Furthermore, the processing element could include a processor or a computer processor, and processing elements may be distributed and/or included in a single device.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A method of assessing a chemical pathway, reaction, and molecule for a chemical retro-synthesis, the method implemented in silico in a processor of a data processing apparatus and comprising the steps of:

receiving, by the processor, input data including at least one chemical pathway, at least one reaction, and at least one molecule;

processing the input data to identify, by the processor and in the input data, structural and chemical features of the at least one chemical pathway, the at least one reaction, and the at least one molecule;

extracting, by the processor, a feature from the features identified in the processed input data;

obtaining, by the processor, an association measure coefficient (AMC) based on data from a chemical knowledgebase including known chemical pathways, reactions, and molecules, wherein obtaining the AMC comprises:

extracting, by the processor, a feature from the chemical knowledgebase similar to the feature extracted from the features identified in the processed input data; and computing, by the processor, the AMC based on the feature extracted from the chemical knowledgebase; and analyzing, by the processor, the processed input data to assess the input data based on the obtained AMC, wherein the analyzing of the processed input data to assess the input data comprises:

assigning, based on the obtained AMC, a score to at least one feature extracted from the features identified in the processed input data;

ranking, based on the assigned score, the at least one chemical pathway, the at least one reaction, and the at least one molecule, included in the input data; and selecting at least one of: a chemical pathway, a reaction, and a molecule for the chemical retro-synthesis.

2. The method of claim 1, wherein the processing of input data comprises at least one of:

identifying a reaction transformation for the at least one reaction included in the input data, and classifying the at least one reaction included in the input data based on an at least one reaction transformation type;

identifying a molecular transformation for the at least one molecule included in the input data, and classifying the at least one molecule included in the input data based on an at least one molecular transformation type; and identifying a molecular substructure contained in the at least one molecule included in the input data.

3. The method of claim 2, wherein:

the processing of input data comprises: the identifying a molecular transformation for the at least one molecule included in the input data, and the classifying the at least one molecule included in the input data based on an at least one molecular transformation type; and the molecular transformation, for the at least one molecule included in the input data, comprises at least one molecule substructure residing on the at least one molecule included in the input data and at least one of a bond change, a bond rearrangement, and a chemical state change that occurs during a reaction process on the at least one molecule included in the input data.

4. The method of claim 2, wherein:

the processing of input data comprises: the identifying a reaction transformation for the at least one reaction included in the input data, and the classifying the at least one reaction included in the input data based on an at least one reaction transformation type; and the reaction transformation, for the at least one reaction included in the input data, comprises a set of molecular transformations of the at least one molecule participating in a reaction included in the input data.

5. The method of claim 1, wherein the feature extracted from the features identified in the processed input data comprises an association of a molecular substructure, an association of a molecular sub structure classified according to a molecular transformation type, and an association of a reaction transformation type.

6. The method of claim 5, wherein the association of a molecular substructure, in the feature extracted from the processed input data, is derived from at least one of an occurrence of at least one molecular substructure and a co-occurrence of the at least one molecular substructure, wherein the co-occurrence is recorded with a relative distance between the molecular substructures.

7. The method of claim 5, wherein the association of a reaction transformation type, in the feature extracted from the processed input data, is derived from at least one of an occurrence of at least one reaction transformation type and a co-occurrence of the at least one reaction transformation type.

8. The method of claim 1, wherein:

the obtaining of an AMC based on data from a chemical knowledgebase comprises processing the chemical knowledgebase to identify, by the processor and in the data of the chemical knowledgebase, structural and chemical features of the known chemical pathways, reactions, and molecules;

the feature extracted from the chemical knowledgebase contains at least one of an association of a molecular substructure, an association of a molecular substructure classified according to a molecular transformation type, and an association of a reaction transformation type; and the computing of the AMC comprises computing the AMC based on the feature extracted from the processed chemical knowledgebase and the feature extracted from the processed input data.

9. The method of claim 8, wherein the processing of the chemical knowledgebase comprises at least one of:

identifying a reaction transformation for at least one reaction included in the chemical knowledgebase and classifying the at least one reaction based on at least one reaction transformation type;

identifying a molecular transformation for at least one molecule included in the chemical knowledgebase and classifying the at least one molecule based on at least one molecular transformation type; and identifying a molecular substructure contained in the at least one molecule included in the chemical knowledgebase.

10. The method of claim 9, wherein:

the processing of the chemical knowledgebase comprises: the identifying a molecular transformation for at least one molecule included in the chemical knowledgebase, and the classifying the at least one molecule based on at least one molecular transformation type; and the molecular transformation, for the at least one molecule included in the chemical knowledgebase, comprises at least one molecule substructure residing on the at least one molecule included in the chemical knowledgebase and at least one of a bond change, a bond rearrangement, and a chemical state change that occurs during a reaction process on the at least one molecule included in the chemical knowledgebase.

11. The method of claim 9, wherein:

the processing of the chemical knowledgebase comprises: identifying a reaction transformation for at least one reaction included in the chemical knowledgebase and classifying the at least one reaction based on at least one reaction transformation type; and the reaction transformation, for the at least one reaction included in the chemical knowledgebase, comprises a set of molecular transformations of the at least one molecule participating in a reaction included in the chemical knowledgebase.

12. The method of claim 8, wherein the association of a molecular substructure, in the feature extracted from the chemical knowledgebase, is derived from at least one of an occurrence of at least one molecular substructure and a co-occurrence of the at least one molecular substructure, wherein the co-occurrence is recorded with a relative distance between the molecular substructures.

13. The method of claim 8, wherein the association of a reaction transformation type, in the feature extracted from the chemical knowledgebase, is derived from at least one of an occurrence of at least one reaction transformation type and a co-occurrence of the at least one reaction transformation type.

14. The method claim 1, wherein the analyzing of the input data to assess the input data further comprises:

computing, by the processor, a composite score, based on the assigned score, for at least one of: the at least one chemical pathway, the at least one reaction, and the at least one molecule included in the input data.

15. The method of claim 14, wherein the analyzing of the input data to assess the input data further comprises:

assigning, by the processor, a rank, according to the computed composite score, to the at least one of: the at least one chemical pathway, the at least one reaction, and the at least one molecule, included in the input data.

16. The method of claim 1, wherein the analyzing of the input data to assess the input data further comprises assigning a rank to at least one feature extracted from the features identified in the processed input data based on a propensity of the at least one feature to occur or exist in the chemical knowledgebase, and wherein the assigning of a rank facilitates the selecting of the at least one of: the chemical pathway, the reaction, and the molecule for the chemical retro-synthesis.

17. The method of claim 1, wherein the analyzing of the input data to assess the input data further comprises filtering, based on the assigned score, at least one of: a chemical pathway, a reaction, and a molecule, in the input data.

18. The method of claim 17, wherein:

the analyzing of the input data to assess the input data further comprises: computing, by the processor, a composite score, based on the assigned score, for at least one of: the at least one chemical pathway, the at least one reaction, and the at least one molecule, included in the input data; and the filtering is performed by selecting at least one of: a chemical pathway, a reaction, and a molecule, in the input data having a computed composite score meeting or exceeding a defined threshold value.

19. A data processing apparatus for assessing, in silico, a chemical pathway, reaction, and molecule for a chemical retro-synthesis, the apparatus comprising:

at least one processor; and a memory operatively coupled to the at least one processor, the memory storing program instructions which, when executed by the at least one processor, cause the processor to:

receive input data including at least one chemical pathway, at least one reaction, and at least one molecule;

process the input data to identify, in the input data, structural and chemical features of the at least one chemical, the at least one reaction, and the at least one molecule;

extract a feature from the features identified in the processed input data;

obtain an association measure coefficient (AMC) based on data from a chemical knowledgebase including known chemical pathways, reactions, and molecules, wherein to obtain the AMC, the program instructions further cause the at least one processor to:

extract a feature from the chemical knowledgebase similar to the feature extracted from the features identified in the processed input data; and compute the AMC based on the feature extracted from the chemical knowledgebase; and analyze the processed input data to assess the input data based on the obtained AMC, wherein to analyze the processed input data to assess the input data, the program instructions further cause the at least one processor to:

assign, based on the obtained AMC, a score to at least one feature extracted from the features identified in the processed input data;

rank, based on the assigned score, the at least one chemical pathway, the at least one reaction, and the at least one molecule, included in the input data; and select at least one of: a chemical pathway, a reaction, and a molecule for the chemical retro-synthesis.

20. A non-transitory computer-readable recording medium having recorded thereon a program for causing a processor to execute a method of assessing, in silico, a feasibility of a chemical pathway, reaction, and molecule for a chemical retro-synthesis, by:

receiving input data including at least one chemical pathway, at least one reaction, and at least one molecule;

processing the input data to identify, in the input data, structural and chemical features of the at least one chemical pathway, the at least one reaction, and the at least one molecule;

extracting a feature from the features identified in the processed input data;

obtaining an association measure coefficient (AMC) based on data from a chemical knowledgebase including known chemical pathways, reactions, and molecules, wherein obtaining the AMC comprises:

extracting a feature from the chemical knowledgebase similar to the feature extracted from the features identified in the processed input data; and computing the AMC based on the feature extracted from the chemical knowledgebase; and analyzing the processed input data to assess the input data based on the obtained AMC, wherein analyzing the processed input data to assess the input data comprises:

assigning, based on the obtained AMC, a score to at least one feature extracted from the features identified in the processed input data;

ranking, based on the assigned score, the at least one chemical pathway, the at least one reaction, and the at least one molecule, included in the input data; and selecting at least one of: a chemical pathway, a reaction, and a molecule for the chemical retro-synthesis.

\* \* \* \* \*